US012661376B2

(12) United States Patent
Liang et al.

(10) Patent No.: US 12,661,376 B2
(45) Date of Patent: Jun. 23, 2026

(54) OPTIMIZED CELL TRANSPLANT, AND PREPARATION METHOD AND USE THEREOF

(71) Applicant: Gwo Xi Stem Cell Applied Technology Co., Ltd., Zhubei (TW)

(72) Inventors: Ruei-Yue Liang, Zhubei (TW); Kai-Ling Zhang, Zhubei (TW); Ming-Hsi Chuang, Zhubei (TW); Po-Cheng Lin, Zhubei (TW); Peggy Leh Jiunn Wong, Zhubei (TW); Chia-Hsin Lee, Zhubei (TW)

(73) Assignee: Gwo Xi Stem Cell Applied Technology Co., Ltd., Zhubei (TW)

( * ) Notice: Subject to any disclaimer, the term of this patent is extended or adjusted under 35 U.S.C. 154(b) by 695 days.

(21) Appl. No.: 17/993,823

(22) Filed: Nov. 23, 2022

(65) Prior Publication Data

US 2024/0075071 A1     Mar. 7, 2024

(30) Foreign Application Priority Data

Aug. 23, 2022     (TW) .................................. 111131594

(51) Int. Cl.
*A61K 35/28*          (2015.01)
*C12N 5/0775*         (2010.01)

(52) U.S. Cl.
CPC ............ *A61K 35/28* (2013.01); *C12N 5/0667* (2013.01); *C12N 2500/32* (2013.01); *C12N 2500/38* (2013.01); *C12N 2500/60* (2013.01); *C12N 2500/90* (2013.01); *C12N 2501/115* (2013.01); *C12N 2501/15* (2013.01)

(58) Field of Classification Search
None
See application file for complete search history.

(56) References Cited

U.S. PATENT DOCUMENTS

2022/0106562 A1*   4/2022   Brodie .................... A61K 35/30
2022/0251516 A1*   8/2022   Rajesh ................ C12N 5/0075

OTHER PUBLICATIONS

Dubey et al., Deducing Insulin-Producing Cells from Goat Adipose Tissue-Derived Mesenchymal Stem Cells, 2022, Cellular Reprogramming, vol. 24, p. 195-203 (Year: 2022).*

* cited by examiner

*Primary Examiner* — Tracy Vivlemore
*Assistant Examiner* — Hanna Marie Thueson

(57) ABSTRACT

Disclosed in the present invention is an optimized cell transplant. The optimized cell transplant is formed by performing gene induction and modification on a mesenchymal stem cell in the form of a small molecule and protein composition. The expression levels of CD200 gene, Galectin-9 gene and VISTA gene can be increased synchronously after cell culture. Vector virus infection and plasmid transfection are not required in the cell preparation process, so that high biological safety and great clinical application value of cells are achieved. The optimized cell transplant is suitable for the technical field of mesenchymal stem cells applied to cell transplantation therapy, and the therapeutic effect of the optimized cell transplant is more excellent than that of the non-modified mesenchymal stem cell.

6 Claims, 5 Drawing Sheets
Specification includes a Sequence Listing.

Group 1 : Control
Group 2 : STZ + Normal saline
Group 3 : STZ + MSCs
Group 4 : STZ + MSCs -plus

* P<0.05
** p<0.01
*** p<0.001

OPTIMIZED CELL TRANSPLANT, AND PREPARATION METHOD AND USE THEREOF

CROSS-REFERENCE TO RELATED APPLICATION

The present application claims priority from Taiwanese Patent Application No. 111131594 filed on Aug. 23, 2022, the contents of which are incorporated herein by reference in their entirety.

REFERENCE TO SEQUENCE LISTING

This application includes a Sequence Listing filed electronically as an XML file named "22PV0071US-1.xml", created on Nov. 19, 2025, with a size of 3,868 bytes. The Sequence Listing is incorporated herein by reference.

BACKGROUND OF THE INVENTION

1. Field of the Invention

The present invention relates to the field of cell therapy, and in particular to an optimized cell transplant, and a preparation method and a use thereof.

2. Description of the Related Art

Cell therapy is to introduce one's own cells (autologous) or other people's cells (allogeneic) into a patient after in vitro culture and proliferation or processing procedures, thereby achieving the purpose of treating or preventing diseases. Many studies have shown that mesenchymal stem cells (MSCs) can effectively treat various diseases, such as hepatic injury, renal injury, knee osteoarthritis, stroke, diabetes and like that have not been cured by specific medicines. It is obvious that mesenchymal stem cell therapy has the potential to meet medical needs.

However, various factors will affect the therapeutic effect in the cell transplantation process. The survival rate of cells transplanted into a recipient will determine treatment outcomes. In particular, in allogeneic cell transplantation, the survival rate of cells is easily affected due to killing by immune cells and phagocytosis in the recipient, thereby reducing the therapeutic effect. Therefore, the survival rate of transplanted cells can only be prolonged by taking immunosuppressants after transplantation to reduce host immune attack. However, long-term use of the immunosuppressants will increase the risks of infection, malignant tumors, cardiovascular diseases and myelosuppression.

At present, studies have indicated that if transplanted cells can highly express CD200 gene, they have the ability of reducing the phagocytosis of host macrophages, so that the survival rate of the transplanted cells can be increased. In addition, high expression of Galectin-9 or VISTA gene can reduce the killing by host T cells, so that the survival rate of the transplanted cells is increased, and the immune infiltration response is reduced, thereby improving the therapeutic effect of the transplanted cells. However, in order to achieve the above effects, in existing methods, gene overexpression is required for cells to increase the expression of specific genes, but gene editing must be performed by vector virus infection or plasmid transfection. Therefore, mutation is easily generated due to virus or plasmid insertion into host DNA. Moreover, if different genes are to be changed simultaneously in the same cell, multiple virus vector infections or plasmid transfections are required, thereby greatly reducing the efficiency and safety of clinical application. These problems are issues that urgently need to be clarified and overcome at present.

SUMMARY OF THE INVENTION

Therefore, the applicant proposes an optimized cell transplant and a preparation method thereof to solve the above problems and further improve the therapeutic ability of a cell transplant in vivo.

That is, the present invention can provide a preparation method of an optimized cell transplant, for preparing an optimized cell transplant with high survival rate and simultaneous high expression of multiple genes. The preparation method includes the following steps: a cell modified culture step: mesenchymal stem cells are cultured in a first medium at a cell density of 6,000-15,000 cells/cm$^2$, where the surface of a culture dish used has an oxygen-containing functional group and thus features a net negative surface charge due and hydrophilic; the first medium is removed after a first culture time to obtain a modified cell intermediate; and a cell optimized culture step: the modified cell intermediate is cultured in a second medium, and the second medium is removed after a second culture time to obtain an optimized cell transplant.

In one embodiment of the present invention, the mesenchymal stem cells are any one selected from adipose-derived stem cells, bone marrow stem cells, peripheral blood stem cells and umbilical cord blood stem cells.

In one embodiment of the present invention, the first culture time is between 1 day and 3 days; and the second culture time is between 7 days and 10 days.

In one embodiment of the present invention, the survival rate of the optimized cell transplant is 90% or more.

In one embodiment of the present invention, the first medium is a serum-free DMEM/F12 medium comprising TGF-b1, FGF-2, hydrocortisone, human serum albumin, L-glutamine, leucine aminopeptidase, an HEPES buffer and lipid.

In one embodiment of the present invention, the second medium is a serum-free DMEM/F12 medium comprising nicotinamide, exendin-4, pentagastrin, a B-27 serum-free supplement and an N-2 supplement.

In addition, the present invention can further provide an optimized cell transplant, obtained by performing gene modification culture on mesenchymal stem cells using the above preparation method; and the expression levels of CD200, Galectin-9 and VISTA genes of the optimized cell transplant are at least two times higher than those of the mesenchymal stem cells.

In one embodiment of the present invention, the present invention can further provide a method for improving the efficacy of mesenchymal stem cells for treating diseases, by re-transplanting the optimized cell transplant obtained by performing gene modification culture on mesenchymal stem cells using the forgoing preparation method into a patient for treatment.

In one embodiment of the present invention, the disease is any one of a cardiovascular disease, traumatic disease, lung disease, nervous system disease, immune disease, liver disease, endocrine disease, skin disease, gastrointestinal disease, kidney disease, hematological disease, cancer or tumor disease, gynecological disease, mental disease, urinary system disease, ophthalmic disease and dental disease.

DETAILED DESCRIPTION OF THE PREFERRED EMBODIMENTS

Figure 1:
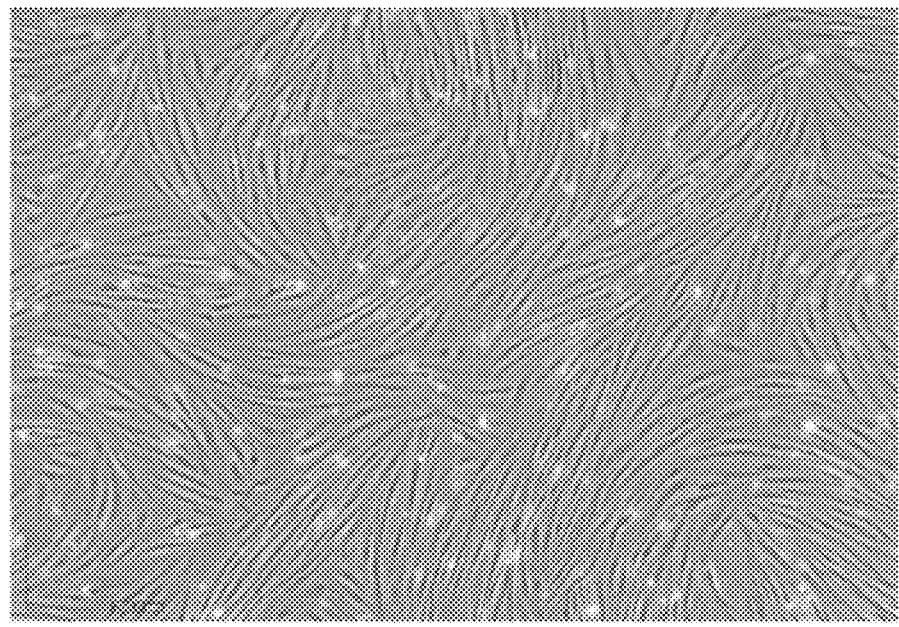
FIG. 1 is an appearance schematic diagram of an optimized cell transplant of the present invention (magnification: 40×).

To make the objectives, technical features and advantages of the present invention better understood by those skilled in the art and to implement the present invention, the technical features and implementations of the present invention are specifically illustrated with reference to the accompanying drawings and are further described by listing preferred embodiments. The following drawings referred to herein are schematic representations of the features of the present invention, and do not and do not need to be completely drawn according to actual situations.

All technical and scientific terms used herein have the same meanings as those generally understood by those of ordinary skill in the art to which the present invention belongs. In addition, unless otherwise clearly contradicted by the context, singular terms used herein should include plural forms, and plural terms should include singular forms.

Although numeral ranges and parameters for defining wide ranges of the present invention are approximate values, related values in specific embodiments have been presented here as accurately as possible. However, any numerical value inevitably contains a standard deviation caused by individual test methods. Here, "about" usually means that an actual value is within plus or minus 10%, 5%, 1% or 0.5% of a specific value or range. Alternatively, the word "about" means that an actual value falls within an acceptable standard error of an average value, depending on the consideration of those of ordinary skill in the art to which the present invention belongs. Except for the embodiments or unless otherwise explicitly stated, it can be understood that all ranges, amounts, values and percentages used herein (for example, those used to describe the use amount of materials, time, temperature, operation conditions, quantitative ratio and the like) are modified by "about". Therefore, unless otherwise stated to the contrary, all the numerical parameters disclosed in this specification and the appended claims are approximate values, and can be changed as required. At a minimum, these numerical parameters should be understood as the indicated significant digits and the values obtained by applying the general carry method.

In order to make the description of the present disclosure more detailed and complete, illustrative description is presented below for aspects and specific embodiments of the present invention, but this is not the only way to implement or apply the specific embodiments of the present invention. The features of multiple specific embodiments, and method steps and the sequence thereof for constructing and operating the specific embodiments are covered in the implementations. However, other specific embodiments may also be used to achieve the same or equal functions and step sequence.

Firstly, a preparation method of an optimized cell transplant provided by the present invention includes the following steps:

A cell modified culture step: mesenchymal stem cells are cultured in a first medium at a cell density of 6,000-15,000 cells/cm$^2$, and the first medium is removed after a first culture time to obtain a modified cell intermediate.

A cell optimized culture step: the modified cell intermediate is cultured in a second medium, and the second medium is removed after a second culture time to obtain an optimized cell transplant.

In the above cell modified culture step, the mesenchymal stem cells are preferably cultured in an adherent culture manner. The cell density of the mesenchymal stem cells inoculated in a culture dish is generally 6,000-15,000 cells/cm$^2$, preferably 6,000-12,000 cells/cm$^2$, more preferably 6,000-10,000 cells/cm$^2$, and most preferably 6,000-8,000 cells/cm$^2$. Furthermore, the first culture time is generally between 1 day and 10 days, preferably between 1 day and 8 days, more preferably between 1 day and 5 days, and most preferably between 1 day and 3 days.

In addition, the surface of the culture dish for bearing the mesenchymal stem cells and the first medium has an oxygen-containing functional group, and is negatively charged and hydrophilic.

According to the technical idea of the present invention, the first medium is a serum-free DMEM/F12 medium including TGF-b1, FGF-2, hydrocortisone, human serum albumin (HSA), L-glutamine, leucine aminopeptidase (LAP), an HEPES buffer and lipid.

Accordingly, the concentration of the TGF-b1 in the first culture is generally between 1 pM and 1 nM, preferably between 10 pM and 1 nM, more preferably between 10 pM and 700 pM, and most preferably between 10 pM and 400 pM.

The concentration of the FGF-2 in the first medium is generally between 1 pM and 1 nM, preferably between 10 pM and 1 nM, more preferably between 10 pM and 700 pM, and most preferably between 10 pM and 400 pM.

The concentration of the hydrocortisone in the first medium is generally between 1 nM and 1 μM, preferably between 10 nM and 1 μM, more preferably between 10 nM and 700 nM, and most preferably between 10 nM and 400 nM.

The concentration of the human serum albumin (HSA) in the first medium is generally between 1 μM and 1 mM, preferably between 1 μM and 700 μM, more preferably between 10 μM and 400 μM, and most preferably between 1 μM and 100 μM.

The concentration of the L-glutamine in the first medium is generally between 1 mM and 100 mM, preferably between 1 mM and 80 mM, more preferably between 1 mM and 60 mM, and most preferably between 1 mM and 40 mM.

The concentration of the leucine aminopeptidase (LAP) in the first medium is generally between 1 μM and 1 mM, preferably between 100 μM and 800 μM, more preferably between 100 μM and 600 μM, and most preferably between 100 μM and 400 μM.

The concentration of the HEPES buffer in the first medium is generally between 1 mM and 100 mM, preferably between 1 mM and 80 mM, more preferably between 1 mM and 60 mM, and most preferably between 1 mM and 40 mM.

The concentration of the lipid in the first medium is generally between 0.05 wt % and 10 wt %, preferably between 0.05 wt % and 8 wt %, more preferably between 0.05 wt % and 6 wt %, and most preferably between 0.05 wt % and 4 wt %.

After the first culture step is completed, it is necessary to remove the first medium in a culture flask to perform the second culture step. In order to prevent the first medium from remaining in the flask, washing the flask may be performed many times with PBS. Furthermore, the second culture time is generally between 7 days and 28 days, preferably between 7 days and 20 days, more preferably between 7 days and 15 days, and most preferably between 7 days and 10 days.

Furthermore, according to the creative idea of the present invention, in the above cell optimized culture step, the second medium is a serum-free DMEM/F12 medium including nicotinamide, exendin-4, pentagastrin, a B-27 serum-free supplement and an N-2 supplement.

The concentration of the nicotinamide in the second medium is generally between 100 μM and 100 mM, preferably between 500 μM and 80 mM, more preferably between 500 μM and 60 mM, and mostly preferably between 500 μM and 40 mM.

The concentration of the exendin-4 in the second medium is generally between 1 nM and 1 μM, preferably between 1 nM and 700 nM, more preferably between 1 nM and 400 nM, and mostly preferably between 1 nM and 100 nM.

The concentration of the pentagastrin in the second medium is generally between 1 nM and 1 μM, preferably between 1 nM and 700 nM, more preferably between 1 nM and 400 nM, and mostly preferably between 1 nM and 100 nM.

The concentration of the B-27 serum-free supplement in the second medium is generally between 0.05 wt % and 10 wt %, preferably between 0.05 wt % and 8 wt %, more preferably between 0.05 wt % and 6 wt %, and mostly preferably between 0.05 wt % and 4 wt %.

The concentration of the N-2 supplement in the second medium is generally between 0.05 wt % and 10 wt %, preferably between 0.05 wt % and 8 wt %, more preferably between 0.05 wt % and 6 wt %, and mostly preferably between 0.05 wt % and 4 wt %.

In addition to the same characteristics as the mesenchymal stem cells, the optimized cell transplant obtained by the cell modified culture step and the cell optimized culture step can highly express CD200 gene, Galectin-9 gene and VISTA gene relative to unmodified mesenchymal stem cells, and can be commonly used in the technical field of mesenchymal stem cells in cell transplantation therapy.

Next, the present invention is described below through specific examples.
Cell Culture Mesenchymal stem cells used in this example were human adipose-derived stem cells (hADSC), and each group was cultured as follows:

First group (control group): mesenchymal stem cells were cultured for 10 days in a Keratinocyte-SFM medium including 5-20 wt % of fetal bovine serum, 1-100 mM of N-acetyl-L-cysteine and 0.05-50 mM of L-ascorbic acid 2-phosphate. The culture environment was a cell incubator with a temperature controlled between 36.5° C. and 38.5° C. and containing 5% carbon dioxide, and the cultured mesenchymal stem cells were referred to as MSCs for short.

Second group (the present invention): mesenchymal stem cells were subjected to cell differentiation culture respectively using a culture dish A and a culture dish B. The polystyrene surface of the culture dish A incorporated an oxygen-containing functional group and thus features a net negative surface charge and hydrophilic, so that the culture dish A had higher hydrophilicity and wettability compared with a general standard tissue culture (TC) treated culture dish, which could promote cell attachment and spreading. The polystyrene surface of the culture dish B was covalently bound to a hydrophilic, neutrally charged hydrogel coating. The hydrogel inhibits specific and nonspecific immobilization, which forces cells into a suspended state that enables 3D spheroid formation.

After differentiation culture, the cells obtained by differentiation in the culture dish A were elongated, the cells obtained by differentiation in the culture dish B took spherical shapes with different sizes, and the survival rate of the cells obtained by differentiation in the culture dish A was at least two times that of the cells obtained by differentiation in the culture dish B. Therefore, the present invention uses the culture dish A for cell differentiation culture.

Mesenchymal stem cells were subjected to cell culture in a first medium for 1 to 3 days, the first medium was removed after the cells were observed to be completely attached to a culture dish, and washing was performed for twice with PBS. Then, cell culture was performed in a second medium for 7 to 10 days, and the cell shapes were observed to become elongated. The culture environment was a cell incubator with a temperature controlled between 36.5° C. and 38.5° C. and containing 5% carbon dioxide, and the cultured optimized cell transplant was referred to as MSCs-plus for short. As shown in FIG. 1, the MSCs-plus cells are elongated in appearance.

The component proportions of the first medium and the second medium are respectively shown in Table 1 and Table 2.

TABLE 1

| Component | Concentration |
| --- | --- |
| Serum-free DMEM/F12 medium | — |
| TGF-b1 | 10 pM to 400 pM |
| FGF-2 | 10 pM to 400 pM |
| Hydrocortisone | 10 nM to 400 nM |
| Human serum albumin (HAS) | 1 μM to 100 μM |
| L-glutamine | 1 mM to 40 mM |
| Leucine aminopeptidase (LAP) | 100 μM to 400 μM |
| HEPES buffer | 1 mM to 40 mM |
| Lipid | 0.05 to 4 wt % |

TABLE 2

| Component | Concentration |
| --- | --- |
| Serum-free DMEM/F12 medium | — |
| Nicotinamide | 500 μM to 40 mM |
| Exendin-4 | 1 nM to 100 nM |
| Pentagastrin | 1 nM to 100 nM |
| B-27 serum-free supplement | 0.05 to 4 wt % |
| N-2 supplement | 0.05 to 4 wt % |

After culture, MSCs and MSCs-plus cells were respectively collected for cell survival rate analysis, gene expression detection analysis, and animal experiments and serum biochemical analysis.

Cell Survival Rate Analysis

The cultured cells in the first group and the second group were respectively collected, and the cell survival rate was counted by an ADAM-MC instrument. It can be known that the survival rate of the MSCs cells in the first group is 93.67±0.58%, and the survival rate of the MSCs-plus cells in the second group is 96.67±1.15%. The two groups maintain a high cell survival rate of 90% or more, and the survival rate of the MSCs-plus cells in the second group is higher.

Gene Expression Detection Analysis

MSCs and MSCs-plus cells were collected, RNA extraction was performed by an RNA extraction kit (Quick-RNA™ MiniPrep, ZYMO RESEARCH), and the specimen was entrusted to Biotechnology Company for a gene expression array experiment. The experiment method was as follows:

In the in vitro transcription process, 0.2 µg of total RNA was amplified by a low input quick-amp labeling kit (Agilent Technologies, USA), and was labeled with Cy3 (CyDye, Agilent Technologies, USA). Then, 0.6 µg of Cy3-labeled CRNA was cultured with a fragmentation buffer at a temperature of 60° C. for 30 min to obtain short fragments with an average size of 50-100 nucleotides.

Then the corresponding fragmented labeled CRNAs were pooled and were hybridized with an Agilent SurePrinte microarray (Agilent Technologies, USA) at a temperature of 65° C. for 17 hours. After being purged with a nitrogen gun and dried, the microarray was scanned by an Agilent microarray scanner (Agilent Technologies, USA) at a wavelength of 535 nm so as to detect the Cy3.

An image obtained through scanning was analyzed by Feature extract 10.7.3.1 software (Agilent Technologies, USA), and the signal and background intensity of each feature were quantized through image analysis and normalization software. Raw signal data was normalized through quantile normalization so as to find differentially expressed genes.

The design of array probes used for various specific genes is shown in Table 3 below.

TABLE 3

| Gene | Probe Sequence | SEQ ID NO |
|---|---|---|
| CD200 | CTGCTTACTGCTTTGCTAATAGCTGGCCTT GCTAGAATCCTTGGTTTCACTGCTGTTCTT | 1 |
| Galectin-9 | TGACCAGAGTGTTCTCTTCAGGGGACTGGC TCCTTTCCCAGTGTCCTTAAAATAAAGAAA | 2 |
| VISTA | AGATCTGTCAACAGGTTAAGTCAATCTGGG GCTTCCACTGCCTGCATTCCAGTCCCAGA | 3 |

Then, the gene expression levels of the MSCs-plus cells relative to the MSCs cells were analyzed and recorded in Table 4.

TABLE 4

| | Gene Expression Level | |
|---|---|---|
| | MSCs cells | MSCs-plus cells |
| CD200 | 1 | 8.45 |
| Galectin-9 | 1 | 2.09 |
| VISTA | 1 | 2.37 |

As shown in Table 4, the expression levels of the CD200 gene, Galectin-9 gene and VISTA gene in the MSCs-plus cells are sequentially 8.45, 2.09 and 2.37 times those in the MSCs cells.

As mentioned in the above prior art, high expression of the CD200 gene can reduce the phagocytic ability of host macrophages and increase the survival rate of the transplanted cells. In addition, high expression of the Galectin-9 and VISTA genes can reduce killing by host T cells, which means that the MSCs-plus cells provided by the present invention can be prevented from being damaged by the macrophages or T cells in vivo when being transplanted into a human body, so that the survival rate of the transplanted cells is increased, and immune infiltration response is reduced, thereby improving the therapeutic effect of the transplanted cells. Animal Experiment and Serum Biochemical Analysis 1. Therapeutic Effect on Renal and Liver Injuries It is known that streptozocin (STZ) is a well-known genotoxic agent, and has been shown to induce DNA injury in rats to lead to oxidative stress so as to induce liver injury and renal injury of the rats.

In this example, the streptozocin (50 mg/kg in citrate buffer, pH 4.5) was continuously applied to 4-to-5-week-old male wistar rats through intraperitoneal injection for 3 days, thereby establishing animal models of liver and renal injuries.

Two weeks after the streptozocin was applied, the rats were divided into groups and transplanted with mesenchymal stem cells through caudal vein. The groups were as follows: first group (Group 1): Control (without application of streptozocin); Group 2: STZ+ Normal Saline; Group 3: STZ+MSCs; and Group 4: STZ+MSCs-plus. There were at least 3 rats in each group, and the transplantation number of cells was $3×10^6/200$ µl normal saline for each rat. Three weeks after one treatment (one injection), blood was drawn for AST, ALT and BUN serum biochemical analysis, and the obtained results were recorded in Table 5.

TABLE 5

| | Serum Biochemical Analysis | | |
|---|---|---|---|
| Group | AST (U/L) | ALT (U/L) | BUN (mg/dL) |
| Group 1 | 91.00 ± 14.21 | 57.50 ± 5.82 | 21.74 ± 1.56 |
| Group 2 | 366.43 ± 99.56 | 232.00 ± 32.08 | 56.03 ± 10.09 |
| Group 3 | 200.10 ± 43.64 | 149.20 ± 50.74 | 39.58 ± 8.61 |
| Group 4 | 145.38 ± 33.50 | 92.80 ± 28.13 | 27.77 ± 7.24 |

Figure 2A:
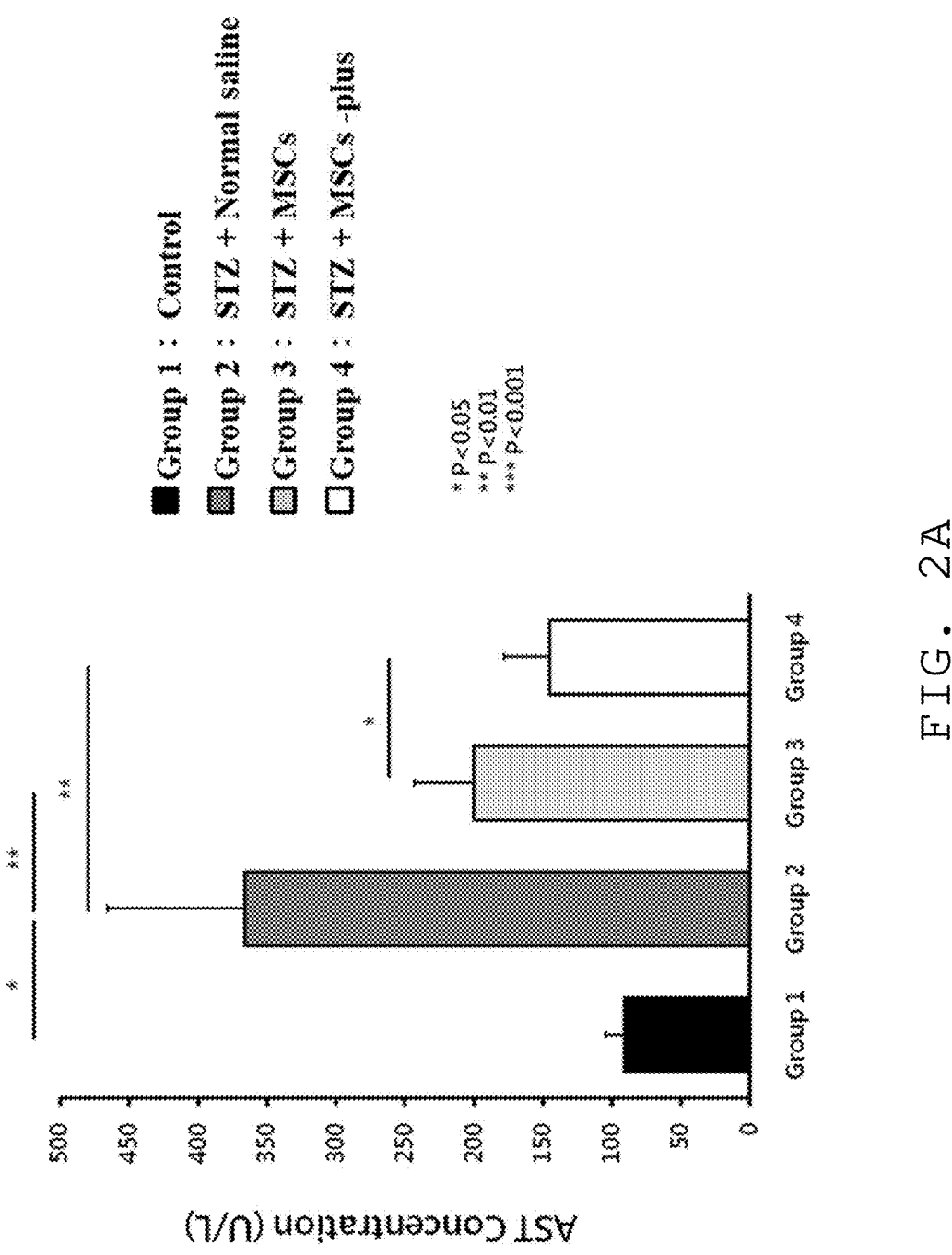
FIG. 2A is a schematic diagram showing comparison between MSCs cells and MSCs-plus cells in reducing liver index AST in animal experiments and serum biochemical analysis.
Figure 2B:
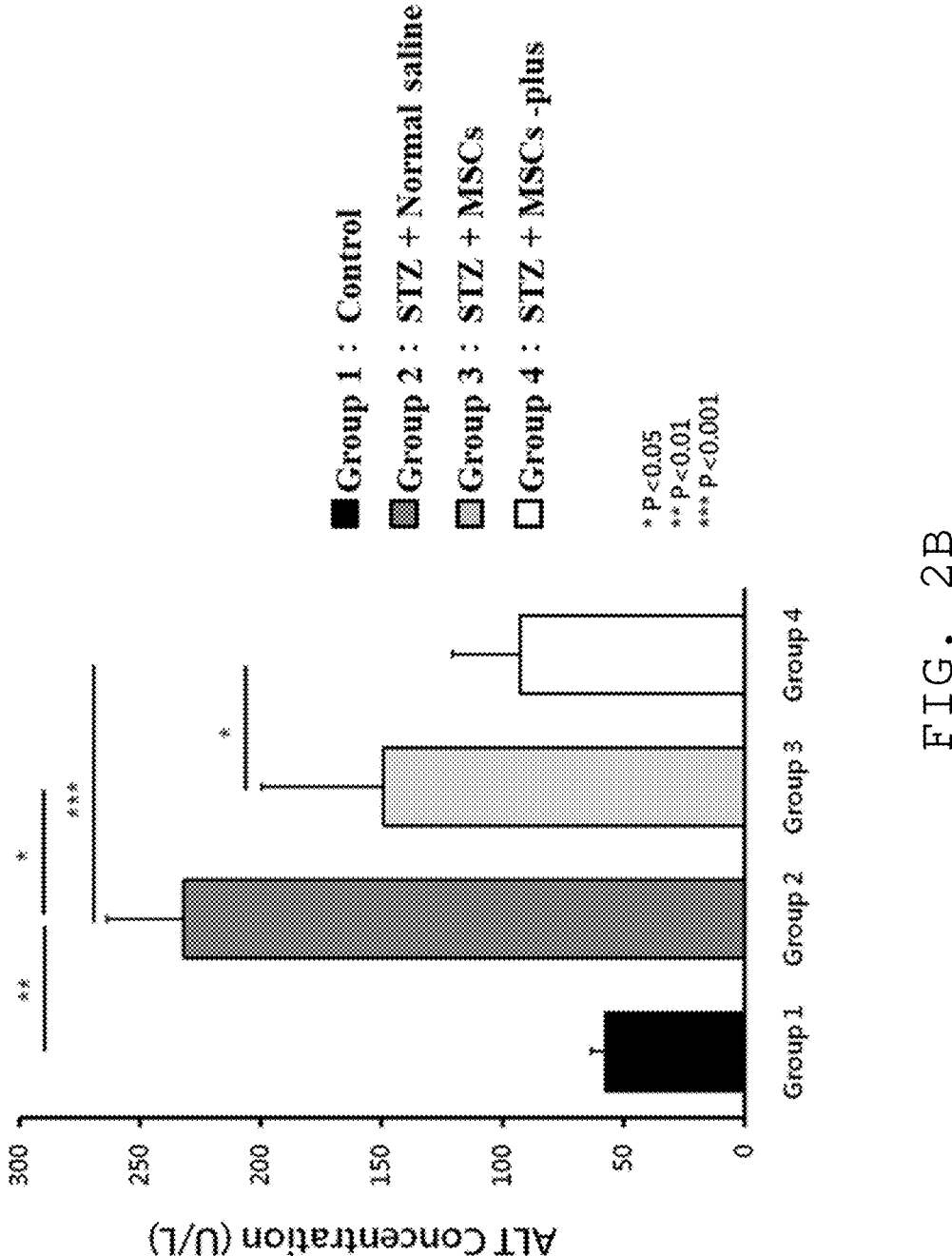
FIG. 2B is a schematic diagram showing comparison between MSCs and MSCs-plus in reducing liver index ALT in animal experiments and serum biochemical analysis.

Taking the effect of mesenchymal stem cells for treating hepatic dysfunction as an example, it can be seen from Table 5, FIG. 2A and FIG. 2B that after the rats are respectively treated by the MSCs cells and the MSCs-plus cells for 21 days, data show that both the MSCs cells and the MSCs-plus cells can significantly reduce liver indexes AST and ALT, and the MSCs-plus cells can exhibit a better therapeutic effect.

Figure 2C:
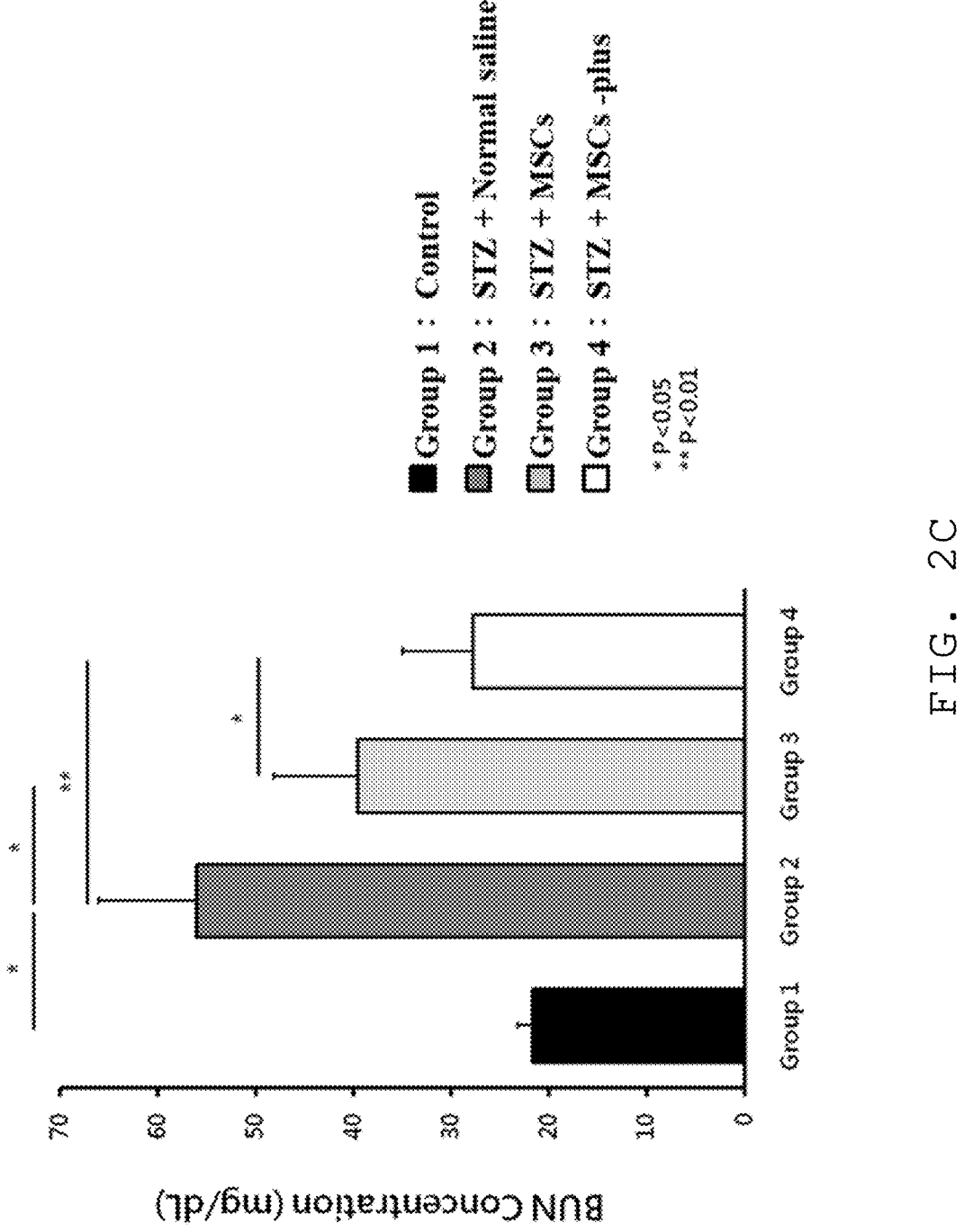
FIG. 2C is a schematic diagram showing comparison between MSCs and MSCs-plus in reducing renal function index BUN in animal experiments and serum biochemical analysis.

Also, taking the effect of mesenchymal stem cells for treating renal dysfunction as an example, it can be seen from Table 5 and FIG. 2C that after the rats were respectively treated by the MSCs cells and the MSCs-plus cells for 21 days, data show that both the MSCs cells and the MSCs-plus cells can significantly reduce renal index BUN, and the MSCs-plus cells can exhibit a better therapeutic effect.

2. Therapeutic Effect on Diabetes

Streptozocin (STZ) is also a well-known compound with specific toxicity on insulin-producing pancreatic β cells in mammalian pancreases. The compound can destroy the pancreatic β cells to increase the blood glucose of animals, and has been widely used to establish animal models of diabetes.

In this example, the streptozocin (50 mg/kg in citrate buffer, pH 4.5) was continuously applied to 4-to-5-week-old male wistar rats through intraperitoneal injection for 3 days, thereby establishing animal models of diabetes.

Two weeks after the streptozocin was applied, the rats were divided into groups and transplanted with mesenchymal stem cells through caudal vein. The groups were as follows: Group 1: Control (without application of streptozocin); Group 2: STZ+ Normal Saline; Group 3: STZ+ MSCs; and Group 4: STZ+MSCs-plus. There were at least 3 rats in each group, and the transplantation number of cells was $3\times10^6/200$ µl normal saline for each rat. After one treatment (one injection), blood was drawn respectively on the day of injection (Day 0), Day 1, Day 3, Day 5 and Day 7 to detect the blood glucose concentration, and the obtained results were recorded in Table 6.

TABLE 6

| | Blood Glucose Concentration (mg/dL) | | | | |
|---|---|---|---|---|---|
| Group | Day 0 | Day 1 | Day 3 | Day 5 | Day 7 |
| Group 1 | 140.17 ± 19.99 | 122.33 ± 15.71 | 142.67 ± 14.22 | 127.50 ± 34.02 | 148.17 ± 21.95 |
| Group 2 | 591.67 ± 14.98 | 563.83 ± 35.05 | 589.33 ± 21.20 | 566.83 ± 38.33 | 573.17 ± 23.44 |
| Group 3 | 589.33 ± 16.15 | 507.50 ± 34.03 | 572.83 ± 36.21 | 533.17 ± 74.51 | 558.83 ± 48.74 |
| Group 4 | 589.50 ± 25.72 | 502.83 ± 60.44 | 486.83 ± 49.03 | 510.00 ± 57.55 | 503.50 ± 46.72 |

Figure 3:
FIG. 3 is a schematic diagram showing comparison between MSCs and MSCs-plus in reducing blood glucose concentration in animal experiments and serum biochemical analysis.

Taking the effect of mesenchymal stem cells for treating diabetes as an example, it can be seen from Table 6 and FIG. 3 that after the MSCs cells and the MSCs-plus cells are respectively transplanted, both can significantly reduce the blood glucose of the diabetic rats on the first day, and the MSCs-plus cells can maintain the blood glucose reducing ability for 7 days. It is obvious that the MSCs-plus cells obtained by the method of the present invention have a better therapeutic effect.

Also, although in the examples, the effect of the optimized cell transplant provided by the present invention is described based on treatment on renal and liver injuries and treatment on diabetes, but the present invention is not limited to these examples, and all diseases that can be treated by mesenchymal stem cells can be treated by the optimized cell transplant provided by the present invention. For example, the disease may be any one of a cardiovascular disease, traumatic disease, lung disease, nervous system disease, immune disease, liver disease, endocrine disease, skin disease, gastrointestinal disease, kidney disease, hematological disease, cancer or tumor disease, gynecological disease, mental disease, urinary system disease, ophthalmic disease and dental disease, which is not elaborated herein.

As can be seen from the above examples, the present invention provides an optimized cell transplant and a preparation thereof. The optimized cell transplant is formed by performing gene induction on a mesenchymal stem cell in the form of a small molecule and protein composition. The expression levels of CD200 gene, Galectin-9 gene and VISTA gene can be increased synchronously after cell culture. Vector virus infection and plasmid transfection are not required in the cell preparation process, so high biological safety and great clinical application value of cells are achieved.

In conclusion, the content of the present invention has been illustrated with the above embodiments, but the present invention is not only limited to these examples. Those of ordinary skill in the art to which the present invention belong may perform various changes and modifications without departing from the spirit and scope of the present invention. For example, the technical contents exemplified in the above embodiments are combined or changed to become new embodiments, and these embodiments are certainly regarded as one of the contents of the present invention. Therefore, the scope to be protected in the specification further includes the claims and the defined scope thereof.

REFERENCE NUMERAL DESCRIPTION

None

What is claimed is:

1. A preparation method of an optimized cell transplant, for preparing an optimized cell transplant with high survival rate and simultaneous high expression of multiple genes; the preparation method comprising the following steps:

a cell modified culture step: mesenchymal stem cells are cultured in a first medium at a cell density of 6,000-15,000 cells/cm$^2$, wherein the surface of a culture dish used has an oxygen-containing functional group and thus features a net negative surface charge due and hydrophilic; the first medium is removed after a first culture time to obtain a modified cell intermediate; and a cell optimized culture step: the modified cell intermediate is cultured in a second medium, and the second medium is removed after a second culture time to obtain an optimized cell transplant, wherein the mesenchymal stem cells are any one selected from adipose-derived stem cells, bone marrow stem cells, peripheral blood stem cells and umbilical cord blood stem cells;

the first medium is a serum-free DMEM/F12 medium comprising TGF-b1, FGF-2, hydrocortisone, human serum albumin, L-glutamine, leucine aminopeptidase, an HEPES buffer and lipid;

the first culture time is between 1 day and 10 days;

the second culture time is between 7 days and 28 days;

the optimized cell transplant has simultaneously and highly expressed CD200, Galectin-9 and VISTA genes; and the expression levels of the CD200, Galectin-9 and VISTA genes of the optimized cell transplant are at least two times higher than those of the mesenchymal stem cells.

2. The preparation method of the optimized cell transplant according to claim 1, wherein the expression level of the CD200 gene of the optimized cell transplant is at least 8 times higher than that of the mesenchymal stem cells.

3. The preparation method of the optimized cell transplant according to claim 1, wherein the expression level of the Galectin-9 gene of the optimized cell transplant is at least 2 times higher than that of the mesenchymal stem cells.

4. The preparation method of the optimized cell transplant according to claim 1, wherein the expression level of the VISTA gene of the optimized cell transplant is at least 2 times higher than that of the mesenchymal stem cells.

5. The preparation method of the optimized cell transplant according to claim 1, wherein the survival rate of the optimized cell transplant is 90% or more.

6. The preparation method of the optimized cell transplant according to claim 1, wherein the second medium is a serum-free DMEM/F12 medium comprising nicotinamide, exendin-4, pentagastrin, a B-27 serum-free supplement and an N-2 supplement.

*    *    *    *    *

SEQUENCE LISTING

```
Sequence total quantity: 3
SEQ ID NO: 1              moltype = RNA  length = 60
FEATURE                   Location/Qualifiers
source                    1..60
                          mol_type = other RNA
                          organism = synthetic construct
SEQUENCE: 1
ctgcttactg ctttgctaat agctggcctt gctagaatcc ttggtttcac tgctgttctt   60

SEQ ID NO: 2              moltype = RNA  length = 60
FEATURE                   Location/Qualifiers
source                    1..60
                          mol_type = other RNA
                          organism = synthetic construct
SEQUENCE: 2
tgaccagagt gttctcttca ggggactggc tcctttccca gtgtccttaa aataaagaaa   60

SEQ ID NO: 3              moltype = RNA  length = 60
FEATURE                   Location/Qualifiers
source                    1..60
                          mol_type = other RNA
                          organism = synthetic construct
SEQUENCE: 3
agatctgtca acaggttaag tcaatctggg gcttccactg cctgcattcc agtccccaga   60
```